(12) United States Patent
Kubota et al.

(10) Patent No.: US 6,509,298 B2
(45) Date of Patent: Jan. 21, 2003

(54) ARTHROPOD-CONTROLLING COMPOSITION

(75) Inventors: Shunichi Kubota, Minoo (JP); Michihiko Fujinami, Minoo (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/956,018

(22) Filed: Sep. 20, 2001

(65) Prior Publication Data

US 2002/0173541 A1 Nov. 21, 2002

(30) Foreign Application Priority Data

Apr. 4, 2001 (JP) ........................................ 2001-105598

(51) Int. Cl.[7] ............................................... A01N 43/16
(52) U.S. Cl. ...................................... 504/292; 549/291
(58) Field of Search .................. 549/291; 424/DIG. 10; 504/292

(56) References Cited

FOREIGN PATENT DOCUMENTS

| | | |
|---|---|---|
| EP | 0 841 063 | 5/1998 |
| JP | 51-19126 | 2/1976 |
| JP | 10-130114 | 5/1998 |
| WO | WO 88/10258 | 12/1988 |

OTHER PUBLICATIONS

D. Rijke et al., "Acidic Components in Essential Oils of Costus Root, Pathouli and Olibanum", Phytochemistry, vol. 17, (1978), pp. 1666–1667.

S. Nakahara et al., "Acidic Compounds in Pathouli Oil", Phytochemistry, vol. 14, (1975), 2713–2714.

*Primary Examiner*—Amelia Owens
(74) *Attorney, Agent, or Firm*—Sughrue Mion, PLLC

(57) ABSTRACT

4-Hydroxy-6-methyl-3-(3-methylbutanoyl)-2-pyrone has a rapid controlling effect against arthropods such as Dictyoptera insects (e.g. German cockroach, smokybrown cockroach).

9 Claims, No Drawings

ARTHROPOD-CONTROLLING COMPOSITION

FIELD OF THE INVENTION

The present invention relates to an arthropod-controlling composition.

BACKGROUND OF THE INVENTION

Many arthropod-controlling compositions are on the market at present. However, the objected harmful arthropods have many kinds and the situations for controlling them are in many ways. Therefore, the arthropod-controlling composition having practically high effectiveness and safety is desired.

Though pyrethroid insecticides having rapid knock-down efficacy are excellent agents for controlling harmful arthropods, progress of pyrethroid resistance to some arthropods has been reported in various places recently. Under these circumstances, non-pyrethroid compounds having excellent knock-down efficacy are earnestly desired.

On the other hand, it is known that some α-pyrone compounds are effective for controlling harmful acarina and houseflies in Japanese Unexamined Patent Publication No. sho-51-19126. However, the compounds described in the publication do not necessarily give a sufficient effect.

SUMMARY OF THE INVENTION

The present invention provides 4-hydroxy-6-methyl-3-(3-methylbutanoyl)-2-pyrone shown by the formula:

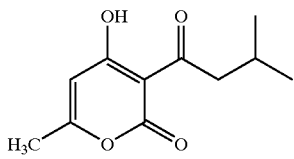

an arthropod-controlling composition comprising it as an active ingredient and a method for controlling arthropods by using it.

DETAILED DESCRIPTION OF THE INVENTION

Examples of the arthropods against which 4-hydroxy-6-methyl-3-(3-methylbutanoyl)-2-pyrone (hereinafter referred as to The Pyrone Compound) exhibits a control effect include the following Insecta, Acarina, Chilognatha, Epimorpha and Isopoda:

Hemiptera Insects:

Delphacidae (planthoppers) such as *Laodelphax striatellus* (small brown planthopper), *Nilaparvata lugens* (brown planthopper), *Sogatella furcifera* (white-backed rice planthopper) and so on; Deltocephalidae (leafhoppers) such as *Nephotettix cincticeps* (green rice leafhopper), *Recilia dorsalis* (zig-zag rice leaf hopper), *Nephotettix virescens* (green rice leafhopper) and so on; Aphididae (aphids); stink bugs; Aleyrodidae (whiteflies); scales; Tingidae (lace bugs); Psyllidae (suckers) and so on.

Lepidoptera Insects:

Pyralidae such as *Chilo suppressalis* (rice stem borer), *Cnaphalocrocis medinalis* (rice leafroller), *Plodia interpunctella* (Indian meal moth) and so on; Noctuidae such as *Spodoptera litura* (tobacco cutworm), *Pseudaletia separata* (rice armyworm), *Mamestra brassicae* (cabbage armyworm) and so on; Pieridae such as *Pieris rapae crucivora* (common cabbageworm) and so on; Tortricidae such as Adoxophyes spp. and so on; Carposinidae; Lyonetiidae; Lymantriidae; Plusiinae; Agrotis spp. such as *Agrotis segetum* (turnip cutworm), *Agrotis ipsilon* (black cutworm) and so on; Helicoverpa spp.; Heliothis spp.; *Plutella xylostella*; *Parnara guttata* (rice skipper); *Tinea pellionella* (casemaking clothes moth);*Tineola bisselliella* (webbing clothes moth) and so on.

Diptera Insects:

Culex spp. such as *Culex pipiens pallens* (common mosquito), *Culex tritaeniorhynchus* and so on, Aedes spp. such as *Aedes aegypti*, *Aedes albopictus* and so on; Anopheles spp. such as *Anopheles sinensis* and so on; Chironomidae (midges); Muscidae such as *Musca domestica* (housefly), *Muscina stabulans* (false stablefly), *Fannia canicularis* (little housefly) and so on; Calliphoridae; Sarcophagidae; Anthomyiidae such as *Delia platura* (seedcorn maggot), *Delia antiqua* (onion maggot) and so on; Tephritidae (fluit flies); Drosophilidae; Psychodidae (moth flies); Tabanidae; Simuliidae (black flies); Stomoxyidae (stable flies); Phoridae; Ceratopogonidae (biting midges) and so on.

Coleoptera Insects (Beetles)

Corn rootworms such as *Diabrotica virgifera* (western corn rootworm), *Diabrotica undecimpunctata howardi* (southern corn rootworm) and so on; Scarabaeidae (scarabs) such as *Anomala cuprea* (cupreous chafer), *Anomala rufocuprea* (soybean beetle) and so on; Curculionidae (weevils) such as *Sitophilus zeamais* (maize weevil), *Lissorhoptrus oryzophilus* (ricewater weevil), ball weevil, *Callosobruchus chinensis* (adzuki bean weevil) and so on; Dermestidae such as *Authrenus verbasci* (varied carpet beetle), *Attagenus unicolor japonicus* (black carpet beetle) and so on; Tenebrionidae (darkling beetles) such as *Tenebrio molitor* (yellow mealworm), *Tribolium castaneum* (red flour beetle) and so on; Chrysomelidae (leaf beetles) such as *Oulema oryzae* (rice leaf beetle), *Phyllotreta striolata* (striped flea beetle), *Aulacophora femoralis* (cucurbit leaf beetle) and so on; Anobiidae; Epilachna spp. such as *Epilachna vigintioctopunctata* (twenty-eight-spotted ladybird) and so on; Lyctidae (powderpost beetles), Bostrychidae (false powderpost beetles), Cerambycidae, *Paederus fuscipes* (robe beetle) and so on.

Dictyoptera Insects:

*Blattella germanica* (German cockroach); *Periplaneta fuliginosa* (smokybrown cockroach); *Periplaneta americana* (American cockroach); *Periplaneta brunnea* (brown cockroach); *Blatta orientalis* (oriental cockroach) and so on.

Thysanoptera Insects (Thrips):

*Thrips palmi*, *Flankliniella occidentalis* (western flower thrips), *Thrips hawaiiensis* (flower thrips) and so on.

Hymenoptera Insects:

Formicidae (ants); Vespidae (hornets); Polistes spp. (long-legged wasps); Bethylidae; Tenthredinidae (sawflies) such as *Athalis rosae ruficornis* (cabbage sawfly) and so on.

Orthoptera Insects:

Gryllotalpidae (mole crickets); Acrididae (grasshoppers) and so on.

Siphonaptera Insects (Fleas):

*Ctenocephalides canis* (dog flea); *Ctenocephalides felis* (cat flea); *Pulex irritans*; and so on.

Anoplura Insects (Lice):

*Pediculus corporis* (body louse); *Pediculus humanus* (head louse); *Pthirus pubis* (crab louse) and so on.

Isoptera Insects:

*Reticulitermes speratus*; *Coptotermes formosanus* (Formosan subterranean termite); and so on.

Harmful Acarina:

Ixodidae (Ticks):

Boophilus microplus; Haemaphysalis longiconis and so on Tetranychidae (spider mites):

Tetranychus cinnabarinus (carmine spider mite); Tetranychus urticae (two-spotted spider mite); Tetranychus kanzawai (Kanzawa spider mite); Panonychus citri (citrus red mite); Panonychus ulmi (European red mite) and so on.

House-dust Mites:

Acaridae such as Tyrophagus putrescentiae(copra mite), Aleuroglyphus ovatus (brown legged grain mite) and so on; Dermanyssidae such as Dermatophagoides farinae (American house dust mite), Dermatophagoides pteronyssinus and so on; Glycyphagidae such as Glycyphagus privatus, Glycyphagus domesticus, Glycyphagus destructor and so on; Cheyletidae such as Chelacaropsis malaccensis, Cheyletus fortis and so on; Tarsonemidae; Chortoglyphus spp.; Haplochthonius spp. and so on.

Chilognatha (millipedes) such as Oxydus spp.; Chilopoda (centipedes) such as red centipede; wood lice such as Porcellio spp., Porcellionides spp.; and pill bugs such as Armadillidium spp. ;and so on.

As The Pyrone Compound, which is an active ingredient of the present controlling agent, gives an efficacy by contacting the objective harmful arthropods including insects and acarina, it is usually to be formulated as described below for use.

Namely, The Pyrone Compound or its solution can be formulated to the present controlling agent such as oil solution, emulsifiable concentrate, wettable powder, flowable (aqueous suspension or aqueous emulsion), granule, dust and so on, by mixing with solid carrier, liquid carrier or liquefied gaseous carrier and optionally surfactant, the other formulation auxiliaries.

The present controlling agent described above contains usually 0.001 to 95% by weight of The Pyrone Compound as an active ingredient.

Examples of the solid carrier used in the formulation described above include fine granules or granules of inorganic carriers such as clays (e.g. kaolin clay, diatomaceous earth, synthetic hydrated silicon oxide, bentonite, Fubasami clay, acid clay, etc.), talc, ceramics, sericite, quartz, calcium carbonate and so on; synthetic resins such as polyethylene, polypropylene and so on; and carriers originated from plants such as wood powder, activated carbon and so on. Examples of the liquid carrier include water, alcohols (e.g. methanol, ethanol, higher alcohols, etc.), ketones (e.g. acetone, methyl ethyl ketone, etc.), aromatic hydrocarbons (e.g. benzene, toluene, xylene, ethylbenzene, methylnaphthalene, etc.), aliphatic hydrocarbons (e.g. hexane, cyclohexane, kerosene, gas oil, etc.), esters (ethyl acetate, butyl acetate, etc.), nitriles (e.g. acetonitrile, isobutyronitrile, etc.), ethers (e.g. diisopropyl ether, dioxane, etc.), acid amides (e.g. N,N-dimethylformamide, N,N-dimethylacetamide, etc.), halogenated hydrocarbons (e.g. dichloromethane, trichloroethane, carbon tetrachloride, etc.), dimethyl sulfoxide, vegetable oils (e.g. soybean oil, cottonseed oil, etc.) and so on. Examples of the liquefied gaseous carrier include fluorocarbon, fluorohydrocarbon, LPG (liquefied petroleum gas), dimethyl ether and carbon dioxide and so on.

Examples of the surfactant optionally used in the formulation include alkyl sulfate salts, alkylsulfonate salts, alkylarylsulfonate salts, alkyl aryl ethers, polyoxyethylenealkyl aryl ethers, polyethylene glycol ethers, polyhydric alcohol esters and sugar alcohol derivatives and so on.

The other formulation auxiliaries are exemplified by sticking agent, dispersant, stabilizer and so on. Examples of sticking agent and dispersant include casein, gelatin, polysaccharides (e.g. starch powder, gum arabic, cellulose derivatives, alginic acid etc.), lignin derivatives, bentonite, sugars and synthetic water-soluble polymers (e.g. polyvinyl alcohol, polyvinylpyrrolidone, polyacrylic acids, etc.). Examples of stabilizer include phenol type antioxidants such as BHT (2,6-di-tert-butyl-4-methyphenol), BHA (mixture of 2-tert-butyl-4-methoxyphenol and 3-tert-butyl-4-methoxyphenol), amine type antioxidants such as diphenylamine, organic sulfur type antioxidants such as 2-mercaptobenzimidazole, PAP (acid isopropyl phosphate), vegetable oils, mineral oils, surfactants, fatty acids, esters of fatty acid and so on.

The flowable formulations (aqueous suspension or aqueous emulsion) usually comprise The Pyrone Compound, dispersant, suspension assistant (for example, protective colloid or a compound giving thixotropy), suitable auxiliaries (for example, antifoamer, rust preventive agent, stabilizer, developing agent, penetrating assistant, antifreezing agent, bactericide, fungicide, etc.) and water. Examples of the protective colloid include gelatin, casein, gums, cellulose ethers, polyvinyl alcohol and so on, and examples of the compound giving thixotropy include bentonite, aluminum magnesium silicate, xanthan gum, polyacrylic acids and so on. Use of the oil which can rarely dissolve The Pyrone Compound in place of water can give suspension-in-oil formulation.

The formulations of emulsifiable concentrate, wettable powder, flowable and so on obtained above are usually diluted with water and so on, and applied at 0.1 to 10000 ppm of the concentration of The Pyrone Compound. The formulations of oil solution, granule, dust and so on are usually applied to harmful arthropods by distributing or spraying as they are.

Further, The Pyrone Compound or its formulation can be used after making the forms below.

A mixture of The Pyrone Compound or its liquid formulation and a propellant can be charged into a pressure container with a spray nozzle to afford an aerosol of the present controlling agent. Further, The Pyrone Compound or its liquid formulation can be impregnated into a base material of mosquito-coil, mosquito-mat, ceramic board and so on to afford a heating volatile formulation such as mosquito-coil and mosquito-mat for electric heater; a heating fumigant formulation such as self-combustible fumigant, chemical reaction type fumigant and porous ceramic board fumigant; a non-heating volatile formulation such as resin volatile formulation and paper volatile formulation; a smoking formulation such as fogging; and an ULV formulation of the present controlling agent. Furthermore, a liquid formulation of The Pyrone Compound can be charged into a container with an absorptive wick in the upper part to afford a bottle containing insecticidal liquid for volitilization by heating the absorptive wick.

These present controlling agents include The Pyrone Compound as an active ingredient in an amount of 0.001% to 95% by weight.

Examples of the propellant for aerosols include propane, butane, isobutane, dimethyl ether, methyl ethyl ether and methylal.

An example of the base material of the mosquito-coil is a mixture of raw plant powder such as wood powder and Pyrethrum marc and a binding agent like Tabu powder (powder of Machilus thunbergii), starch or gluten.

An example of the base material of the mosquito-mat for electric heating fumigation is a plate of compacted fibrils of cotton linters or a mixture of pulp and cotton linters.

The base material of the self-combustible fumigant includes, for example, an exothermic agent (e.g. nitrate, nitrite, guanidine salt, potassium chlorate, nitrocellulose, ethylcellulose, wood powder, etc.), a pyrolytic stimulating agent (e.g. alkali metal salt, alkaline earth metal salt, dichromate, chromate, etc.), an oxygen source (e.g. potassium nitrate, etc.), a combustion assistant (e.g. melanin, wheat starch, etc.), a bulk filler (e.g. diatomaceous earth, etc.) and a binding agent (e.g. synthetic glue, etc.).

The base material of the chemical reaction type fumigant includes, for example, an exothermic agent (e.g. alkali metal sulfide, polysulfide, hydrogensufide and hydrated salt, calcium oxide, etc.), a catalytic agent (e.g. carbonaceous substance, iron carbide, activated clay, etc.), an organic foaming agent (e.g. azodicarbonamide, benzenesulfonylhydrazide, dinitrosopentamethylenetetramine, polystyrene, polyurethane, etc.) and a filler (e.g. natural or synthetic fibers, etc.).

An example of the base material of the resin volatile formulation is thermoplastic resin, and examples of the base material of the paper volatile formulation include filter paper and Japanese paper.

The present controlling agent can be used simultaneously with the other insecticide, the other acaricide, repellent or synergist under non-mixed conditions or pre-mixed conditions.

Examples of the insecticides and acaricides include organophosphorus compounds such as fenitrothion [O,O-dimethyl O-(3-methyl-4-nitrophenyl)phosphorothioate], fenthion [O,O-dimethyl O-(3-methyl-4-(methythio)phenyl) phosphorothioate], diazinon [O,O-diethyl O-2-isopropyl-6-methylpyrimidin-4-yl phosphorothioate], chlorpyrifos [O,O-diethyl O-3,5,6-trichloro-2-pyridyl phosphorothioate], DDVP [2,2-dichlorovinyl dimethyl phosphate], cyanophos [O-4-cyanophenyl O,O-dimethyl phosphorothioate], dimethoate [O,O-dimethyl S-(N-methylcarbamoylmethyl) dithiophosphate], phenthoate[ethyl2-dimethoxyphosphinothioylthio(phenyl)acetate], malathion [diethyl(dimethoxyphosphinothioylthio)succinate], and azinphos-methyl [S-3,4-dihydro-4-oxo-1,2,3-benzotriazin-3-ylmethyl O,O-dimethyl phosphorodithioate];carbamate compounds such as BPMC (2-sec-butylphenyl methylcarbamate), benfracarb [ethyl N-[2,3-dihydro-2,2-dimethylbenzofuran-7-yloxycarbonyl (methyl)aminothio]-N-isopropyl-β-alaninate], propoxur [2-isopropoxyphenyl N-methylcarbamate] and carbaryl [1-naphthyl N-methylcarbamate]; pyrethroid compounds such as etofenprox [2-(4-ethoxyphenyl)-2-methylpropyl-3-phenoxybenzyl ether], fenvalerate [(RS)-α-cyano-3-phenoxybenzyl (RS)-2-(4-chlorophenyl)-3-methyl-butyrate], esfenvalerate [(S)-α-cyano-3-phenoxybenzyl (S)-2-(4-chlorophenyl)-3-methylbutyrate], fenpropathrin [(RS)-α-cyano-3-phenoxybenzyl2,2,3,3-tetramethylcyclopropanecarboxylate], cypermethrin [(RS)-α-cyano-3-phenoxybenzyl (1RS)-cis,trans-3-(2,2-dichlorovinyl)-2,2-dimethylcyclopropanecarboxylate], permethrin [3-phenoxybenzyl (1RS)-cis,trans-3-(2,2-dichlorovinyl)-2,2-dimethylcyclopropanecarboxylate], cyhalothrin [(RS)-α-cyano-3-phenoxybenzyl(Z)-(1RS)-cis-3-(2-chloro-3,3,3-trifluoroprop-1-enyl)-2,2-dimethylcyclopropanecarboxylate], deltamethrin [(S)-α-cyano-3-phenoxybenzyl(1R)-cis-3-(2,2-dibromovinyl)-2,2-dimethylcyclopropanecarboxylate], cycloprothrin [(RS)-α-cyano-3-phenoxybenzyl (RS)-2,2-dichloro-1-(4-ethoxyphenyl)cyclopropanecarboxylate], fluvalinate[α-cyano-3-phenoxybenzyl N-(2-chloro-α,α,α-trifluoro-p-tolyl)-D-valinate], bifenthrin [2-methylbiphenyl-3-ylmethyl (Z)-(1RS)-cis-3-(2-chloro-3,3,3-trifluoroprop-1-enyl)-2,2-dimethylcyclopropanecarboxylate], 2-methyl-2-(4-bromodifluoromethoxyphenyl)propyl 3-phenoxybenzyl ether, tralomethrin [(S)-α-cyano-3-phenoxybenzyl(1R-cis)-3-{(1RS)(1,2,2,2-tetrabromoethyl)}-2,2-dimethylcyclopropanecarboxylate], silafluofen[(4-ethoxyphenyl){3-(4-fluoro-3-phenoxyphenyl)propyl}dimethylsilane], d-phenothrin [3-phenoxybenzyl (1R-cis, trans)-chrysanthemate], cyphenothrin[(RS)-α-cyano-3-phenoxybenzyl (1R-cis, trans)-chrysanthemate], d-resmethrin[5-benzyl-3-furylmethyl (1R-cis,trans)-chrysanthemate], acrinathrin [(S)-α-cyano-3-phenoxybenzyl(1R,cis(Z))-2,2-dimethyl-3-{3-oxo-3-(1,1,1,3,3,3-hexafluoropropyloxy)propenyl}cyclopropanecarboxylate], cyfluthrin[(RS)-α-cyano-4-fluoro-3-phenoxybenzyl 3-(2,2-dichlorovinyl)-2,2-dimethylcyclopropanecarboxylate], tefluthrin [2,3,5,6-tetrafluoro-4-methylbenzyl (1RS-cis(Z))-3-(2-chloro-3,3,3-trifluoroprop-1-enyl)-2,2-dimethylcyclopropanecarboxylate], transiluthrin [2,3,5,6-tetrafluorobenzyl (1R-trans)-3-(2,2-dichlorovinyl)-2,2-dimethylcyclopropanecarboxylate], tetramethrin [3,4,5,6-tetrahydrophthalimidomethyl (1RS)-cis,trans-chrysanthemate], allethrin [(RS)-3-allyl-2-methyl-4-oxocyclopent-2-enyl (1RS)-cis,trans-chrysanthemate], prallethrin [(S)-2-methyl-4-oxo-3-(2-propynyl) cyclopent-2-enyl (1R)-cis,trans-chrysanthemate], empenthrin [(RS)-1-ethynyl-2-methyl-2-pentenyl (1R)-cis,trans-chrysanthemate], imiprothrin [2,5-dioxo-3-(prop-2-ynyl) imidazolidin-1-ylmethyl (1R)-cis,trans-2,2-dimethyl-3-(2-methylprop-1-enyl)cyclopropanecarboxylate], d-furamethrin [5-(2-propynyl)furfuryl (1R)-cis,trans-chrysanthemate] and 5-(2-propynyl)furfuryl 2,2,3,3-tetramethylcyclopropanecarboxylate; nitroimidazolidine derivatives such as imidacloprid (1-(6-chloro-3-pyridylmethyl)-N-nitroimidazolidin-2-ylideneamine); N-cyanoamidine derivatives such as N-cyano-N'-methyl-N'-(6-chloro-3-pyridylmethyl) acetamidine; nitenpyram [N-(6-chloro-3-pyridylmethyl)-N-ethyl-N'-methyl-2-nitrovynylidenediamine]; thiacloprid [1-(2-chloro-5-pyridylmethyl)-2-cyanoiminothiazoline]; thiamethoxam [3-((2-chloro-5-thiazolyl)methyl)-5-methyl-4-nitroiminotetrahydro-1,3,5-oxadiazine]; 1-methyl-2-nitro-3-((3-tetrahydrofuryl)methyl)guanidine; 1-(2-chloro-5-thiazolyl)methyl-3-methyl-2-nitroguanidine; nitroiminohexahydro-1,3,5-triazine derivatives; chlorinated hydrocarbons such as endosulfan [6,7,8,9,10,10-hexachloro-1,5,5a,6,9,9a-hexahydro-6,9-methano-2,4,3-benzodioxathiepine oxide], γ-BHC [1,2,3,4,5,6-hexachlorocyclohexane] and 1,1-bis(chlorophenyl)-2,2,2-trichloroethanol; benzoylphenylurea compounds such as chlorfluazuron [1-(3,5-dichloro-4-(3-chloro-5-trifluoromethylpyridyn-2-yloxy)phenyl)-3-(2,6-difluorobenzoyl)urea], teflubenzuron [1-(3,5-dichloro-2,4-difluorophenyl)-3-(2,6-difluorobenzoyl)urea] and flufenoxuron [1-(4-(2-chloro-4-trifluoromethylphenoxy)-2-fluorophenyl)-3-(2,6-difluorobenzoyl)urea]; juvenile hormone like compounds such as pyriproxyfen [4-phenoxyphenyl2-(2-pyridyloxy)propyl ether], methoprene [isopropyl (2E,4E)-11-methoxy-3,7,11-trimethyl-2,4-dodecadienoate] and hydroprene [ethyl (2E,4E)-11-methoxy-3,7,11-trimethyl-2,4-dodecadienoate]; thiourea derivatives such as diafenthiuron [N-(2,6-diisopropyl-4-phenoxyphenyl)-N'-tert-butylcarbodiimide]; phenylpyrazole compounds; 4-bromo-2-(4-chlorophenyl)-1-ethoxymethyl-5-trifluoromethylpyrrol-3-carbonitrile

[chlorfenapil]; metoxadiazone [5-methoxy-3-(2-methoxyphenyl)-1,3,4-oxadiazol-2(3H)-one], bromopropylate [isopropyl 4,4'-dibromobenzilate], tetradifon [4-chlorophenyl 2,4,5-trichlorophenyl sulfone], chinomethionat [S,S-6-methylquinoxaline-2,3-diyldithiocarbonate], pyridaben [2-tert-butyl-5-(4-tert-butylbenzylthio)-4-chloropyridazin-3(2H)-one], fenpyroximate [tert-butyl (E)-4-[(1,3-dimethyl-5-phenoxypyrazol-4-yl)methyleneaminooxymethyl]benzoate], tebufenpyrad [N-(4-tert-butylbenzyl)-4-chloro-3-ethyl-1-methyl-5-pyrazolecarboxamide], polynactins complex [tetranactin, dinactin and trinactin], pyrimidifen [5-chloro-N-[2-{4-(2-ethoxyethyl)-2,3-dimethylphenoxy}ethyl]-6-ethylpyrimidin-4-amine], milbemectin, abamectin, ivermectin and azadirachtin [AZAD]. Examples of the synergists include bis-(2,3,3,3-tetrachloropropyl) ether (S-421), N-(2-ethylhexylbicyclo[2.2.1]hept-5-ene-2,3-dicarboximide (MGK-264) and α-[2-(2-butoxyethoxy)ethoxy] -4,5-methylenedioxy-2-propyltoluene (piperonyl butoxide).

The application amount and concentration of the present controlling agent can be suitably designed according to the type of the formulations, time, place, and method of application, kind of noxious pests and damage.

EXAMPLES

The present invention will be further illustrated in more details by the production examples and test examples, although the present invention is not limited in any sense to these examples. Parts represent parts by weight in the following examples.

Production Example 1

Twenty parts of The Pyrone Compound are dissolves in 65 parts of xylene, mixed with 15 parts of emulsifier Sorpol 3005X (registered trademark of Toho Chemical Co., Ltd.), and stirred sufficiently to give 20% emulusifiable concentrate.

Production Example 2

Forty parts of The Pyrone Compound are mixed first with 5 parts of Sorpol 5060 (registered trademark of Toho Chemical Co., Ltd.) and then with 32 parts of Carplex #80 (registered trademark of Shionogi & Co., Ltd.; fine powder of synthetic hydrated silicon oxide) and 23 parts of 300-mesh diatomaceous earth, and stirred with a juice mixer to give 40% wettable powder.

Production Example 3

One and a half (1.5) parts of The Pyrone Compound are mixed with 98.5 parts of AGSORB LVM-MS 24/48 (granular carrier of calcined montmorillonite having the particle diameter of 24- to 48-mesh provided by OIL DRI Corp.) sufficiently to give 1.5% granule.

Production Example 4

A mixture of 10 parts of The Pyrone Compound, 10 parts of phenylxylylethane and 0.5 part of Sumidule L-75 (tolylenediisocyanate provided by Sumika Bayer Urethane Co., Ltd.) is added to 20 parts of a 10% aqueous solution of gum arabic, and stirred with a homomixer to give an emulsion having the mean particle diameter of 20 μm. The emulsion is further mixed with 2 parts of ethylene glycol and allowed to react on a water bath of 60° C. for 24 hours to give a microcapsule slurry. On the other hand, a thicking agent solution is prepared by dispersing 0.2 part of xanthan gum and 1.0 part of Veegum R (aluminum magnesium silicate provided by Sanyo Chemical Co., Ltd.) in 56.3 parts of ion-exchanged water.

Forty-two and a half parts (42.5 parts) of the above microcapsule slurry and 57.5 parts of the above thicking agent solution are mixed to give 10% microencapsulated formulation.

Production Example 5

A mixture of 10 parts of The Pyrone Compound and 10 parts of phenylxylylethane is added to 30 parts of a 10% aqueous solution of polyvinyl alcohol and stirred with a homomixer to give an emulsion having the mean particle diameter of 3 μm. On the other hand, a thicking agent solution is prepared by dispersing 0.2 part of xanthan gum and 0.4 part of Veegum R (aluminum magnesium silicate provided by Sanyo Chemical Co., Ltd.) in 49.4 parts of ion-exchanged water.

Fifty parts of the above emulsion and 50 parts of the above thicking agent solution are mixed to give 10% flowable formulation.

Production Example 6

Five parts of The Pyrone Compound are mixed with 3 parts of Carplex #80 (registered trademark of Shionogi & Co., Ltd.; fine powder of synthetic hydrated silicon oxide), 0.3 parts of PAP and 91.7 parts of 300-mesh talc, and stirred with a juice mixer to give 5% dust.

Production Example 7

A half (0.5) part of The Pyrone Compound was dissolved in 10 parts of dichloromethane and mixed with 89.5 parts of Isoper M (isoparaffin provided by Exxon Chemical Corp.) to give 0.5% oil solution.

Production Example 8

An aerosol vessel was filled with 0.1 g of The Pyrone Compound and 49.9 g of Neotiozol (Chuokasei Company). The vessel was then equipped with a valve, and 25 g of dimethyl ether and 25 g of LPG were charged and shaken. The aerosol vessel was equipped with an actuator and to give oil-based aerosol.

Production Example 9

An aerosol vessel was filled with 0.2 g of The Pyrone Compound and 49.8 g of Neotiozol (Chuokasei Company). The vessel was then equipped with a valve, and 25 g of dimethyl ether and 25 g of LPG were charged and shaken. The aerosol vessel was equipped with an actuator and to give oil-based aerosol.

Production Example 10

An aerosol vessel was filled with 0.4 g of The Pyrone Compound and 49.6 g of Neotiozol (Chuokasei Company). The vessel was then equipped with a valve, and 25 g of dimethyl ether and 25 g of LPG were charged and shaken. The aerosol vessel was equipped with an actuator and to give oil-based aerosol.

Production Example 11

An aerosol vessel was filled with 0.8 g of The Pyrone Compound and 49.2 g of Neotiozol (Chuokasei Company). The vessel was then equipped with a valve, and 25 g of dimethyl ether and 25 g of LPG were charged and shaken.

The aerosol vessel was equipped with an actuator and to give oil-based aerosol.

Production Example 12

An aerosol vessel was filled with 1.6 g of The Pyrone Compound and 48.4 g of Neotiozol (Chuokasei Company). The vessel was then equipped with a valve, and 25 g of dimethyl ether and 25 g of LPG were charged and shaken. The aerosol vessel was equipped with an actuator and to give oil-based aerosol.

Production Example 13

An aerosol vessel is filled with 50 parts of purified water and a dissolved mixture of 0.6 part of The Pyrone Compound, 0.01 part of BHT, 5 parts of xylene, 3.39 parts of deodorized kerosene and 1 part of Atmos 300 (registered trademark of Atlas Chemical Co.). The vessel is then equipped with a valve and 40 parts of propellant (liquefied petroleum gas) is charged through the valve into the aerosol vessel under pressure to give water-based aerosol.

Production Example 14

A solution prepared by dissolving 0.5 g of The Pyrone Compound in 20 ml of acetone is homogeneously mixed with 99.5 g of a carrier for a mosquito-coil (mixture of Tabu powder, Pyrethrum marc and wood powder at the ratio of 4:3:3). After 120 ml of water is added, the mixture is kneaded sufficiently, molded and dried to give mosquito-coil.

Production Example 15

One hundred and twenty grams (120 g) of water dissolving 0.3 g of Malachite Green dye and 0.2 g of sodium dehydroacetate were added to a carrier for a mosquito-coil (mixture of Tabu powder, Pyrethrum marc and wood powder at the ratio of 5:3:2), kneaded sufficiently, molded and dried to give a base material for mosquito-coil. One hundred milligrams (100 mg) of The Pyrone Compound were dissolved in 5 ml of acetone. A quarter milliliter (0.25 ml) of the solution was painted on 0.5 g of the above base material for mosquito-coil and sufficiently air-dried to give 1% mosquito-coil.

Production Example 16

One hundred and twenty grams (120 g) of water dissolving 0.3 g of Malachite Green dye and 0.2 g of sodium dehydroacetate are added to a carrier for a mosquito-coil (mixture of Tabu powder, Pyrethrum marc and wood powder at the ratio of 5:3:2), kneaded sufficiently, molded and dried to give a base material for mosquito-coil. In 0.7 g of deodorized kerosene, 0.3 g of The Pyrone Compound is dissolved. One gram (1 g) of the solution is painted on 29 g of the above base material for mosquito-coil and sufficiently air-dried to give 1% mosquito-coil.

Production Example 17

A solution prepared by dissolving 1g of The Pyrone Compound in 20 ml of acetone is homogeneously mixed with 99 g of a carrier for a mosquito-coil (mixture of Tabu powder, Pyrethrum marc and wood powder at the ratio of 5:3:2) and 120 ml of water dissolving 0.3 g of Malachite Green dye and 0.2 g of sodium dehydroacetate. The mixture is kneaded sufficiently, molded and dried to give mosquito-coil.

Production Example 18

Acetone is added to 0.2 g of The Pyrone Compound, 0.1 g of BHT and 0.4 g of piperonyl butoxide to make the total 10 ml. A hgalf milliliter (0.5 ml) of the obtained solution is impregnated with a base material (a plate of compacted fibrils of a mixture of pulp and cotton linters: 2.5 cm×1.5 cm, 0.3 cm in thickness) for mosquito-mat homogeneously to give a mosquito-mat for electric heater.

Production Example 19

One-fifth part (0.2 part) of The Pyrone Compound and 0.1 part of BHT are dissolved in 99.7 parts of deodorized kerosene to give a solution. The solution is charged in a vessel of polyvinyl chloride. In the vessel is inserted an absorptive wick which is inorganic powder solidified with a binder and then calcined, the upper portion of which wick can be heated with a heater, to give a part of electric heating fumigation device using a liquid.

Production Example 20

A solution prepared by dissolving 100 mg of The Pyrone Compound in an appropriate amount of acetone is impregnated with a porous ceramic plate (4.0 cm×4.0 cm, 1.2 cm in thickness) to give a heating fumigant.

Next, a method for preparing The Pyrone Compound is shown as Reference preparation example.

Reference Preparation Example

Ten grams (10.0 g, 79.3mmol) of 4-hydroxy-6-methyl-2-pyrone were suspended in 100 ml of toluene at room temperature. To the suspension, 1.22 g (10.0 mmol) of N,N-dimethylaminopyridine, 8.79 g (86.1 mmol) of isovaleric acid and 18.5 g (89.7mmol) of dicyclohexylcarbodiimide were added subsequently. The mixed solution was stirred for 1 hour at room temperature, and then heated to 70° C. and stirred for 20 hours under heating. After the mixed solution was allowed to stand at room temperature, the precipitated insoluble dicyclohexylurea was filtered off, and washed with 1N hydrochloric acid once and 10% brine twice. The organic layer was dried over magnesium sulfate and evaporated under reduced pressure to give a crude oily product.

The crude oily product was subjected to silica gel column chromatography (eluent: hexane/ethyl acetate=6/1) to give 7.01 g of The Pyrone Compound (yield 42%).

$^1$H-NMR (CDCl$_3$/TMS): 0.96 (6H, d), 2.22 (1H, m), 2.27 (3H, s), 2.96 (2H, d), 5.93 (1H, s), 16.99 (1H, s).

The effect of the present controlling agent is shown in the following Test Examples. For showing an efficacy of the present controlling agent enough, 4-hydroxy-6-methyl-3-(2-methylpropanoyl-2-pyrone (hereinafter, referred to as Reference compound 1) described in Japanese Unexamined Patent Publication No. sho-51-19126 (Compound No. 3) of the formula:

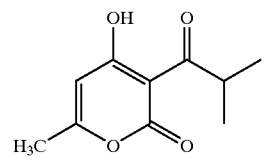

4-hydroxy-6-methyl-3-(2-ethylbutanoyl)-2-pyrone (hereinafter, referred to as Reference compound 2) described in Japanese Unexamined Patent Publication No. sho-51-19126 (Compound No. 5) of the formula:

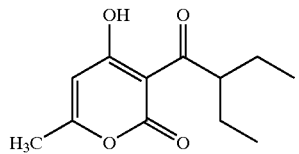

and 4-hydroxy-6-methyl-3-(cyclopropanecarbonyl)-2-pyrone (hereinafter, referred to as Reference compound 3) described in Japanese Unexamined Patent Publication No. sho-51-19126 (Compound No. 11) of the formula:

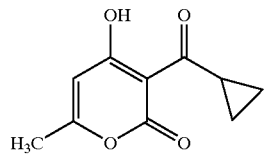

were used as references.

Test example 1

According to Production example 7, each of the 0.5% oil solutions of The Pyrone Compound and Reference compound 1 was prepared.

A square of paper (side: 20 cm) was covered on the iron net set on the bottom of the metallic chamber (46 cm×46 cm, 70 cm in height). A container (8.75 cm in diameter, 7.5 cm in height, having 16-mesh net at the bottom and spreading butter on the wall for preventing escape) was set on the paper. In the container, ten (5 males and 5 females) adult German cockroaches were released. By means of spray gun, 1.5 ml of the above oil solution was applied to the test insects at pressure of $4.1 \times 10^4$ Pa from the upper part of the chamber. The container was taken out of the chamber 30 seconds after spraying and the test insects were transferred to a plastic cup. Two minutes after spraying, the knocked-down cockroaches were counted.

The results are given in Table 1.

TABLE 1

| | Knock-down percentage (%) |
|---|---|
| The Pyrone Compound | 100 |
| Reference compound 1 | 10 |

Test Example 2

According to Production example 7, each of the 0.25% oil solutions of The Pyrone Compound and Reference compounds 2 and 3 was prepared. The same procedures as Test Example 1 gave the knock-down percentages and $KT_{50}$ values (minutes for knocked-down 50% of cockroaches) in Table 2.

TABLE 2

| | Knock-down percentage (%) | $KT_{50}$ (minutes) |
|---|---|---|
| The Pyrone Compound*[1] | 95 | 0.85 |
| Reference compound 2*[2] | 0 | more than 10 |
| Reference compound 3*[2] | 6.7 | more than 10 |

*[1]average of 6 repetitions
*[2]average of 3 repetitions

What is claimed is:

1. 4-Hydroxy-6-methyl-3-(3-methylbutanoyl)-2-pyrone.

2. An arthropod-controlling composition which comprises 4-hydroxy-6-methyl-3-(3-methylbutanoyl)-2-pyrone as an active ingredient, and a carrier.

3. A method for controlling arthropods which comprises applying an effective amount of 4-hydroxy-6-methyl-3-(3-methylbutanoyl)-2-pyrone to arthropods or a place where the arthropods inhabit.

4. A method according to claim 3, wherein the arthropods are insects.

5. A method according to claim 3, wherein the arthropods are cockroaches.

6. The method for controlling arthropods according to claim 3, wherein the 4-hydroxy-6-methyl-3-(3-methylbutanoyl)-2-pyrone is applied with a propellant in the form of an aerosol.

7. The method for controlling arthropods according to claim 3, wherein the 4-hydroxy-6-methyl-3-(3-methylbutanoyl)-2-pyrone is impregnated into a base material of a mosquito-coil, a mosquito-mat, or a ceramic board.

8. The method for controlling arthropods according to claim 3, wherein the 4-hydroxy-6-methyl-3-(3-methylbutanoyl)-2-pyrone is applied as a chemical reaction type fumigant, a porous ceramic board fumigant, a non-heating volatile formulation, a paper volatile formulation, a smoking formulation, or an ULV formulation.

9. The method for controlling arthropods according to claim 3, wherein the 4-hydroxy-6-methyl-3-(3-methylbutanoyl)-2-pyrone is applied with a container having an absorptive wick in which the upper portion of the wick can be heated.

* * * * *